(12) United States Patent
Tang (10) Patent No.: US 10,123,893 B2
(45) Date of Patent: Nov. 13, 2018

(54) PREWIRE CHANNEL STENT (71) Applicant: Lilong Tang, Fuzhou (CN)

(72) Inventor: Lilong Tang, Fuzhou (CN)

( * ) Notice: Subject to any disclaimer, the term of this patent is extended or adjusted under 35 U.S.C. 154(b) by 0 days.

(21) Appl. No.: 14/533,705

(22) Filed: Nov. 5, 2014

(65) Prior Publication Data

US 2015/0182363 A1 Jul. 2, 2015

(30) Foreign Application Priority Data

Dec. 29, 2013 (CN) ..................... 2013 2 0895986 U (51) Int. Cl.
*A61F 2/954* (2013.01)
*A61F 2/958* (2013.01)

(52) U.S. Cl.
CPC ...... *A61F 2/954* (2013.01); *A61F 2002/9583* (2013.01)

(58) Field of Classification Search
CPC .. A61F 2002/9583; A61F 2/954; A61F 2/958; A61F 2/962
USPC ..................... 623/1.11; 604/103.08
See application file for complete search history.

(56) References Cited

U.S. PATENT DOCUMENTS

| | | | | |
|---|---|---|---|---|
| 5,827,321 A * | 10/1998 | Roubin | ...................... | A61F 2/91 606/195 |
| 5,941,895 A * | 8/1999 | Myler | ................... | A61M 29/00 606/195 |
| 6,007,517 A | 12/1999 | Anderson | | |
| 6,290,673 B1 * | 9/2001 | Shanley | .................. | A61F 2/958 604/102.02 |
| 7,524,329 B2 * | 4/2009 | Rucker | ..................... | A61F 2/88 606/192 |
| 2003/0153973 A1 * | 8/2003 | Soun | ........................ | A61F 2/90 623/1.16 |
| 2003/0187494 A1 * | 10/2003 | Loaldi | .................... | A61F 2/856 623/1.11 |
| 2004/0143286 A1 | 7/2004 | Johnson et al. | | |
| 2006/0106448 A1 * | 5/2006 | Shaked | ........... | A61B 17/12022 623/1.11 |
| 2007/0073269 A1 * | 3/2007 | Becker | ................ | A61M 3/0295 604/509 |
| 2008/0114331 A1 * | 5/2008 | Holman | .................. | A61F 2/958 604/509 |
| 2009/0326634 A1 * | 12/2009 | Vardi | ..................... | A61F 2/856 623/1.11 |
| 2012/0089220 A1 | 4/2012 | Lualdi | | |

FOREIGN PATENT DOCUMENTS

DE   297 08 803 U1   7/1997
EP   0 897 700 A1    2/1999

OTHER PUBLICATIONS

European Search Report dated Apr. 27, 2015, in connection with corresponding European Application No. 14197293 (3 pages).

* cited by examiner

*Primary Examiner* — Diane Yabut
*Assistant Examiner* — Erich Herbermann
(74) *Attorney, Agent, or Firm* — Maier & Maier, PLLC (57) ABSTRACT

A prewire channel stent has a structure that includes a balloon having a metallic mesh material outside the balloon, a central passage inside the balloon, and a second passage disposed between the metallic mesh material and the balloon. The second passage allows a second guidewire to be received therein, and the use of the second guidewire thereby avoids the problem of wire exchange and stent dislodgement in known devices.

3 Claims, 10 Drawing Sheets

Conventional Stent

Conventional Stent

FIG.7B

Conventional Stent

FIG.7C

Conventional Stent

FIG.7D

Conventional Stent

FIG.7E

Conventional Stent

FIG.8A

Prewire Channel Stent

FIG.8B

Prewire Channel Stent

FIG.8C

Prewire Channel Stent

FIG.8D

Prewire Channel Stent

FIG.8E

Prewire Channel Stent

PREWIRE CHANNEL STENT

CROSS REFERENCE TO RELATED APPLICATIONS

Not applicable.

STATEMENT REGARDING FEDERALLY SPONSORED RESEARCH OR DEVELOPMENT

Not applicable.

FIELD OF THE INVENTION

The present invention relates generally to a medical device for the treatment of vascular disease.

BACKGROUND OF THE INVENTION

Cardiovascular stents are widely used in the treatment of vascular diseases. For example, stents have been broadly implanted in vessels to treat vessel narrowing, occlusion, aneurysm, and dissection, among other conditions. A typical conventional or known stent contains a metallic mesh material that is mounted or carried on a deflated balloon. In the center of the balloon is a channel, through which a guidewire can pass to facilitate movement through the arteries; however, there is no channel or space between the metallic mesh material and the balloon. A guidewire is inserted to the vessel and pass the location that needs to be treated and then the cardiovascular stent mounted or carried on a deflated balloon is inserted into the vessel and delivered to the desired location through this guidewire to facilitate movement through the arteries. When the stent is at the desired location, the balloon is inflated to expand and, thereby, deploy the stent to support the artery.

Vessels have branches; when narrowing, these narrowed branches are referred to as "bifurcation lesions". When treating a bifurcation lesion with a conventional or known stent, one guidewire is delivered to the main branch, and another guidewire is delivered to a side branch. After the stent is delivered and deployed at a bifurcation lesion, the guidewire in the side branch should be pulled back from the space between the metallic mesh material and the vessel wall and then sent into the main branch through the lumen of the stent. Thereafter, another wire from the main branch should also be pulled back and sent to the side branch through the metallic mesh from the lumen of the stent in the vessel. This procedure is called "wire-exchange". This "wire-exchange" procedure is complicated and time-consuming.

In addition, when an ostial lesion (usually defined as a lesion within 3 mm of the ostium of the vessel at the aorto-ostial or branch-ostial junction) is treated, a typical conventional or known stent has to be deployed precisely at the desired location. To ensure precise deployment at the desired location, some operators like to employ the Szabo technique[1]: specifically, they inflate part of the balloon with low pressure, and then deflate the balloon to allow the guidewire to pass through the space between the metallic mesh material and the balloon for the precise deployment of the stent. However, this procedure has a risk of stent dislodgement[1].

U.S. Pat. No. 8,771,342 issued Jul. 8, 2014 to Vardi is of interest for showing the background of this type of invention, and this reference is hereby incorporated herein in its entirety. In this reference, a method of deploying a stent in a bifurcation is shown that includes introducing two guidewires through the main vessel and using the two guidewires for guiding a dual lumen catheter carrying a stent first to an initial position proximal to the stent deployment position, retracting one wire, and projecting it from the catheter and through a side of the stent a branch guidewire into the second branch vessel, and then moving the catheter to the predetermined deployment position while guided by the main guidewire in the first branch vessel, and the branch guidewire in the second branch vessel. The stent is then expanded, and the catheter is removed with the stent remaining in its deployed position An alternative embodiment includes introducing one wire, advancing the system over the one wire and subsequently introducing the second wire.

U.S. Pat. No. 7,771,462 issued Aug. 10, 2010 to Davidson, et al. is of interest for showing the background of this type of invention, and this reference is hereby incorporated herein in its entirety. This reference describes a designed catheter system comprises a catheter having a catheter body with a distal end, a proximal end, a main vessel guidewire lumen for receiving a main vessel guidewire and a balloon disposing at the distal end of the catheter body. The catheter further includes a side member that is disposed adjacent to the catheter body. The side member has a distal end, a proximal end, and a branch vessel guidewire lumen for receiving a branch vessel guidewire. A stent having a side hole is disposed over the balloon, and a distal portion of the side member is disposed beneath at least a portion of the stent while being adjacent to and movable with respect to the balloon.

U.S. Pat. No. 8,828,071 issued Sep. 9, 2014 to Bourang et al is of interest for showing the background of this type of invention, and this reference is hereby incorporated herein in its entirety. This references discusses a system for treating a bifurcation that includes first and second delivery catheters, each having an expandable member. A stent having a side hole is disposed on the second delivery catheter. A portion of the first delivery catheter is disposed under a portion of the stent. The first delivery catheter is slidable relative to the second delivery catheter, and the first delivery catheter passes through the side hole. Expansion of the first expandable member expands a proximal portion of the stent in a main branch vessel, and expansion of the second expandable member expands a distal portion of the stent in a side branch vessel.

U.S. Pat. No. 8,808,347 issued Aug. 19, 2014 to Bourang et al is of interest for showing alignment of the side branch stent with the main branch stent, and this reference is hereby incorporated herein in its entirety. This reference describes a system for treating a bifurcation includes a first radially expandable stent and a second radially expandable stent. The first stent has a side hole and a plurality of lateral elements extending from the side hole. The second stent has a plurality of axial elements extending away from the proximal end of the second stent. The axial elements of the second stent interdigitate with the lateral elements of the first stent when both stents have been expanded.

U.S. Pat. No. 8,795,347 issued Aug. 5, 2014 to Bourang et al is of interest for showing methods and systems for treating a bifurcation with provisional side branch stenting.

There is a need for a newly designed stent to overcome the shortcomings of the typical conventional or known stent.

SUMMARY OF THE INVENTION

From the foregoing, it is seen that it is a problem in the art to provide a device meeting the above requirements.

According to the present invention, a device is provided which meets the aforementioned requirements and needs in the prior art. Specifically, the device according to the present invention provides a prewire channel stent having a structure that includes a balloon having a metallic mesh material outside the balloon, a central passage with ancillary component to inflate or deflate inside the balloon, and a second passage disposed between the metallic mesh material and the balloon.

Other objects and advantages of the present invention will be more readily apparent from the following detailed description when read in conjunction with the accompanying drawings.

DETAILED DESCRIPTION OF THE INVENTION

Figure 1:
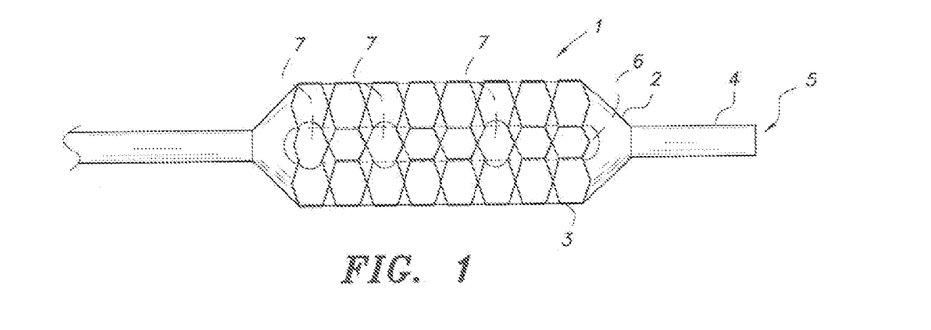
FIG. 1 is a top elevational view of a prewire channel stent in which a balloon is in an inflated status.

FIG. 1 is a top elevational view of a prewire channel stent 1 having an expandable balloon 2, and in which the expandable balloon 2 is in an inflated status. This expandable balloon 2 is in the inflated status during deployment, and is in a deflated status before deployment. A metallic mesh material 3 is premounted or carried on the expandable balloon 2.

Figure 2:
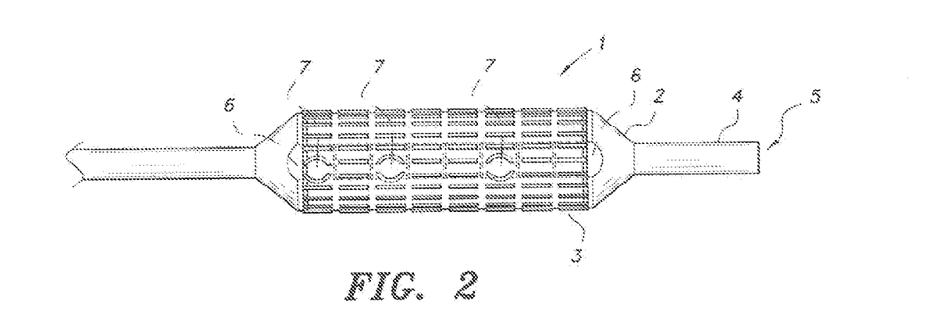
FIG. 2 is a top elevational view of the prewire channel stent of FIG. 1 in which the balloon is in a deflated status.

The metallic mesh material 3 is expanded when the balloon 2 is inflated during deployment, but is in a systolical status when the balloon 2 is deflated (i.e. is in its deflated status) before deployment (FIG. 2). A central catheter 4 goes through the balloon 2, and has a central passage 5 which allows a guidewire 20 (shown in FIG. 6) to go therethrough.

Figure 6:
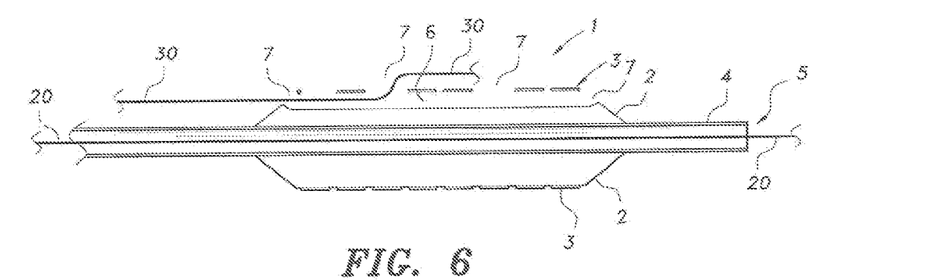
FIG. 6 is a longitudinal cross-sectional view of the prewire channel stent of FIG. 1, wherein the balloon is in the inflated status and a guidewire is in a central passage of a catheter, and another guidewire is in the channel or space.

A channel or space 6 is shown in dashed outline in FIG. 1 and FIG. 2, and is provided between the metallic mesh material 3 and the expandable balloon 2. A plurality of openings 7 (shown in FIGS. 1, 2, 4, and 6) are provided for communication between the channel or space 6 and a region outside the metallic mesh material 3. The openings 7 are formed through the metallic mesh material 3 as shown in FIG. 6. The openings 7 are provided so that the guidewire 30 can pass into the channel or space 6 and then exit through one of the openings 7, as shown in FIG. 6.

Alternative Embodiments and Variations

Alternative or additional embodiments are contemplated as being within the scope of the present invention. In one such embodiment, the channel or space 6 can have a lining 62, for example a tubular lining, through which the wire 30 can pass. In this embodiment, the lining would include openings that correspond to the openings 7. In another such embodiment, the channel or space 6 can be limited in extent such that is passes only partway along the length of the metallic mesh material 3; in a further variation on this embodiment, it is contemplated that fewer openings 7 could be provided than the number shown, so that—for example—only a single such opening 7 is provided. Also, the number of openings 7 is not limited to the number shown and illustrated; more or fewer such openings 7 could be provided, within the scope of the present invention.

In use, one or more guidewires 30 can go through one of the openings 7 and into the channel or space 6 when the metallic mesh material 3 is in the systole status and the balloon 2 is in the deflated status. The channel or space 6 can be substantially closed or—alternatively—can remain open until such time as the metallic mesh material 3 is in the diastolic status and the balloon 2 is in the inflated status.

As seen in FIG. 1, the balloon 2 extends longitudinally along the central catheter 4. The metallic mesh material 3 shown in FIG. 1 surrounds the central region of the balloon 2. The channel or space 6 has the openings 7 disposed as shown, such that the guidewire 30 can enter and leave the channel or space 6 through any two of these openings 7. FIG. 6 illustrates this.

FIG. 2 is a top elevational view of the prewire channel stent 1 of FIG. 1 in which the balloon 2 is in a deflated status. The channel or space 6 has the openings 7 disposed at one and another end and also along the middle of the channel or space 6 as shown in FIG. 2, such that a guidewire can enter and leave the channel or space 6 at the openings 7. The channel or space 6 is shown in dashed outline in FIG. 1 and in FIG. 2, and is provided between the metallic mesh material 3 and the balloon 2.

Figure 3A:
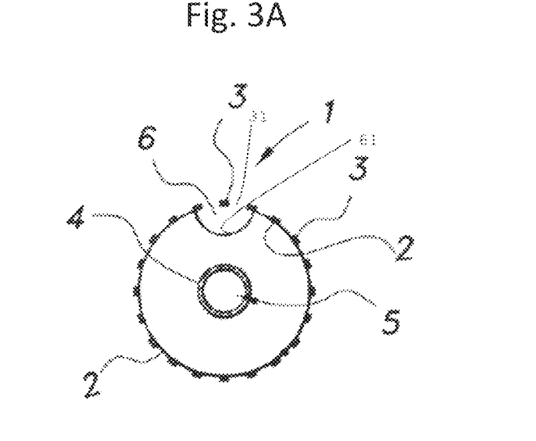
FIG. 3A is a transverse cross-sectional view of the prewire channel stent of FIG. 1 in which the balloon is in the inflated status.
Figure 3B:
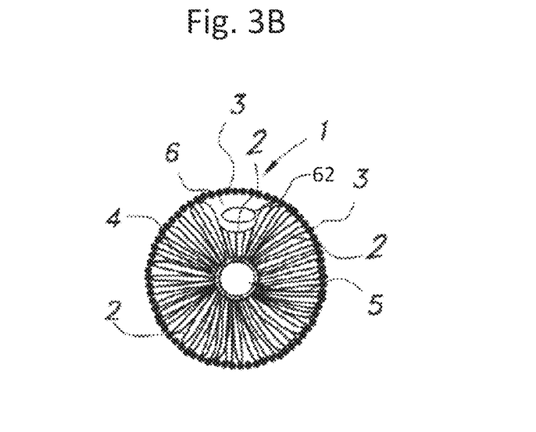
FIG. 3B is a transverse cross-sectional view of the prewire channel stent of FIG. 1 in which the balloon is in the deflated status.

FIG. 3A is a transverse cross-sectional view of the prewire channel stent 1 of FIG. 1 in which the balloon 2 is in the inflated status. The curved surface of the balloon 2 is visible and bounds a lower side of the channel or space 6. The metallic mesh material 3 bounds an upper side of the channel or space 6. The channel or space 6 can be substantially closed, or alternatively can still remain open, when the metallic mesh material 3 is in the diastolic status and the balloon 2 is in the inflated status.

Figure 4:
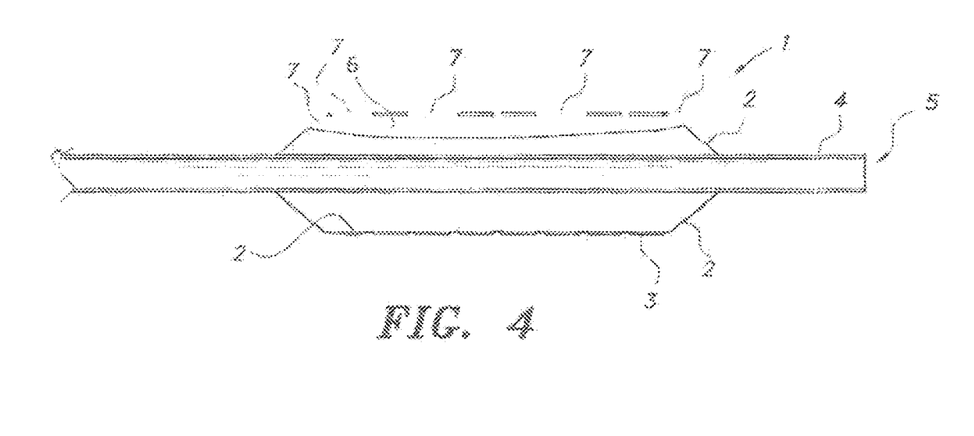
FIG. 4 is a longitudinal cross-sectional view of the prewire channel stent of FIG. 1, wherein the balloon is in the inflated status.

FIG. 4 is a longitudinal cross-sectional view of the prewire channel stent 1 of FIG. 1, wherein the balloon 2 is in the inflated status. This view shows a side view of the channel or space 6. In this view, the curved surface of the balloon 2 is visible and bounds the lower side of the channel or space 6. Also as shown in this view, the metallic mesh material 3 bounds the upper side of the channel or space 6. The channel or space 6 can exist or, alternatively can disappear (i.e. collapse) when the balloon 2 is in the inflated status. Openings 7 exist at both ends of the channel or space 6. More openings can exist between the both ends of the channel or space 6, as shown in the drawings. The channel or space 6 can extend from the end of metallic mesh material to the another end of metallic mesh material.

The terminology channel or space, as used herein, means that the passageway is formed by the element referred to as the channel or space 6, and this passageway can be in the form of a channel formed in the adjacent materials or can be provided as a space between the adjacent materials. The width of the channel or space 6 is selected to be sufficient for passage of the wire 30 therethrough in the manner explained above, and can be relatively thin and narrow or can be relative wide. All such variations are contemplated as being within the scope of the present invention.

Figure 5:
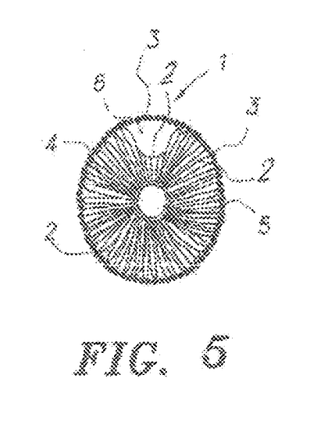
FIG. 5 is a transverse cross-sectional view of the prewire channel stent of FIG. 2 in which the balloon is in the deflated status.

FIG. 5 is a transverse cross-sectional view of the prewire channel stent 1 of FIG. 2 in which the balloon 2 is in the deflated status. The parts shown in this view are those described hereinabove. In this view, the folds of the balloon 2 are visible. The channel or space 6 is shown as being relatively large in this view for the sake of clarity, and is not limited to this specific size or shape shown.

FIG. 6 is a longitudinal cross-sectional view of the prewire channel stent 1 of FIG. 1, wherein the balloon 2 is in the inflated status. This view shows a side view of the channel or space 6 with guidewire 30 going through the channel or space 6 and the guidewire 20 passing through the central passage 5 of the catheter 4. The guidewire 30 can go through any openings 7 of the channel or space 6. The channel or space 6 can be substantially closed, or alternatively can still remain open, when the metallic mesh material 3 is in the diastolic status and the balloon 2 is in the inflated status.

In the above discussion, a guidewire 20 is mentioned. The role of the guidewire 30 is for tracking. When treating the patients, the guidewire 30 is firstly sent to the vessels which are to be treated. Thereafter, a balloon and stent are sent through the guidewire 20 (by tracking) to the desired position of the vessels. All known conventional stents and balloons currently designed have a central channel (corresponding to channel 4 of the present invention) with central passage for the guidewire 20 to go through. However, there is not any channel or space in currently designed stents (referred to herein as conventional stents) that correspond to the channel or space 6 of the present invention which is for another guidewire (i.e., a second guidewire, namely guidewire 30 shown in FIG. 6) between the metallic mesh material 3 and the balloon 2.

Vessels in the human body can be described somewhat like highways in the country which have forks or branches (i.e., bifurcation). In a patient, therefore, if the narrow position is in bifurcation, it is necessary to use two guidewires in each of the branches. So when the stent is sent through the central passage 5 of its central channel 4 by one guidewire in a bifurcation position to release the stent in main branch, then another guidewire in the side branch must be between the metallic mesh material and the vessel wall (in other words, the wire is outside the stent). The guidewire outside the stent in the side branch should be pulled back and then sent to main branch again through the inside stent and the guidewire in original main branches should be pulled back and sent to side branch across the metallic mesh material through the inside stent (or the doctor can send another wire across the metallic mesh material to the side branch through inside the stent). This process is called "wire exchange" which is achieved in the vessels and therefore is complicated and time consuming and sometimes cannot be finished because of the complications that may arise. In the present invention, the channel or space 6 is provided so that the guidewire in the side branch can go across the metallic mesh material through the inside of the stent outside the human body. Therefore, wire exchange is not necessary (i.e. this makes the step of wire exchange unnecessary).

When an ostial lesion is treated, a typical conventional or known stent has to be deployed precisely at the desired location. To ensure precise deployment at the desired location, some operators like to employ the Szabo technique[1]: specifically, they inflate part of the balloon with low pressure, and then deflate the balloon to allow the guidewire to pass through the space between the metallic mesh material and the balloon. However, this procedure has a risk of stent dislodgement[1]. In the present invention, the channel or space 6 is provided to avoid the risk of stent dislodgement.

The lesions involved in the bifurcation of the vessels could have different lengths. The principle of treating such lesions is to use the stent to fully cover the lesions. The channel or space 6 can be a different length from one end of the metallic mesh material 3 of the stent to the another end of metallic mesh material 3. The openings 7 of the channel or space 6 can be provided in multiple locations provided along the channel or space 6. This design allows the guidewire 30 to go across any openings 7 of the channel or space 6 based on the need of the length of the lesion in the vessel.

This stent system can be applied not only in vessels, but also in bronchi, bile ducts, urethrae, esophagi, and other organs or tissues.

Working Examples: Steps for Use of the Prior Device Versus the Present Invention The following illustrates a working example for a conventional stent, shown in FIGS. 7A-7E, and a working example for the Pre-Wire Channel Stent of the present invention, shown in FIGS. 8A-8E.

Figure 7A:
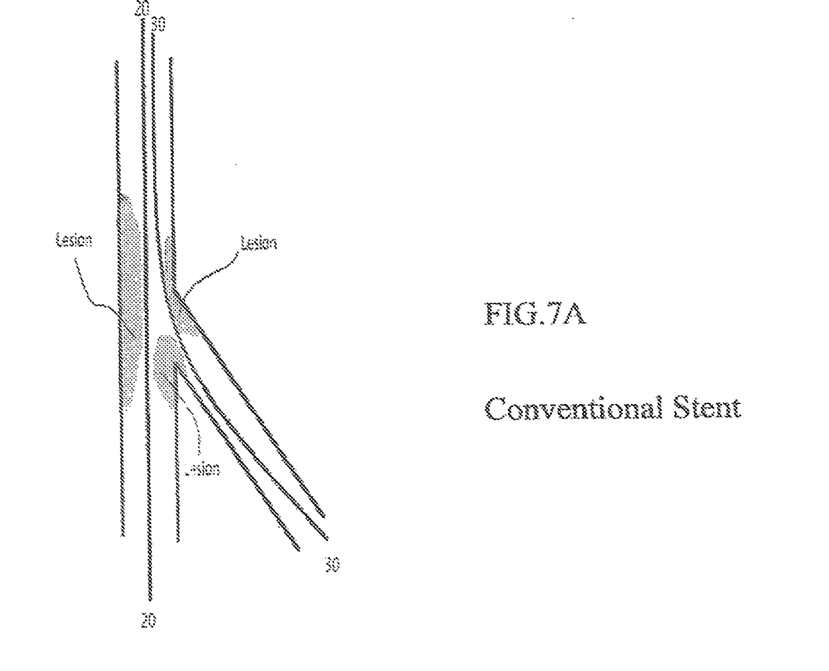
FIGS. 7A-7E illustrate a working example for a conventional stent, and respectively show steps for use of the conventional stent.

The procedures of a conventional or known stent implant for bifurcation lesion in a vessel as explained as follows. Step 1 is shown in FIG. 7A, wherein a guidewire 20 is sent to a main branch and a guidewire 30 is sent to a side branch.

Figure 7B:
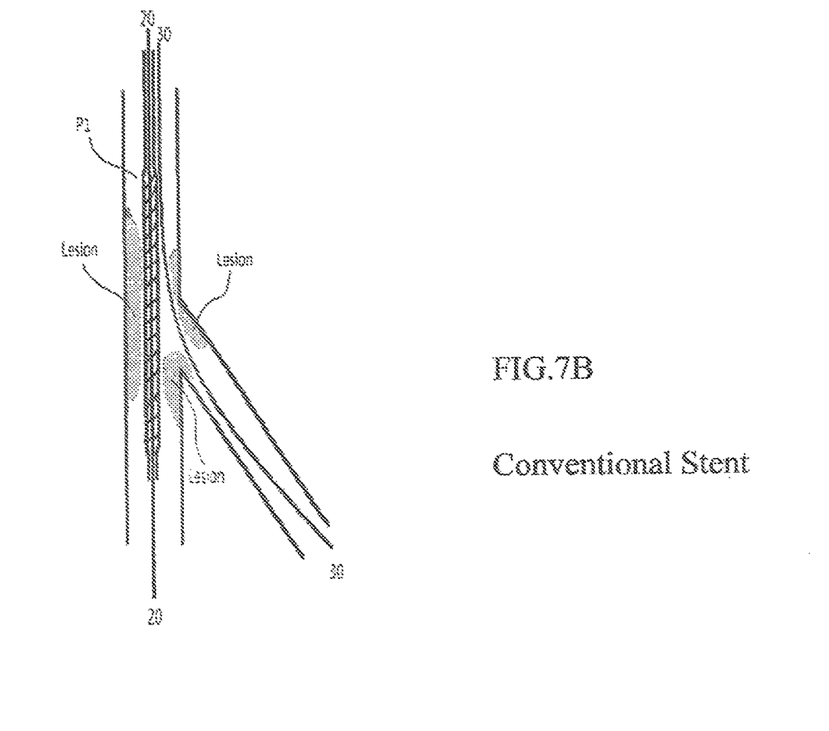

Step 2 is shown in FIG. 7B, wherein a system 1P of a conventional or known stent and balloon is sent through the guidewire 20 (by tracking) to the desired position of the vessels.

Figure 7C:
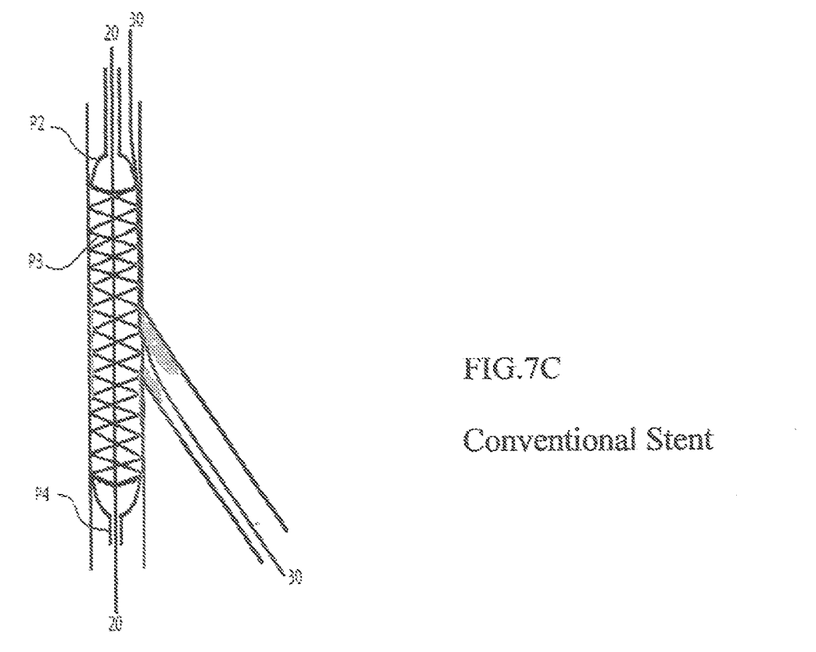

Step 3 is shown in FIG. 7C, a balloon 2P is inflated and a conventional stent 3P is dilated to support the vessel, and the guidewire 20 is still in the main branches through the lumen of the stent and the guidewire 30 is in the side branch through the space between the vessel wall and the metallic mesh material of the stent (i.e., outside the stent).

Figure 7D:
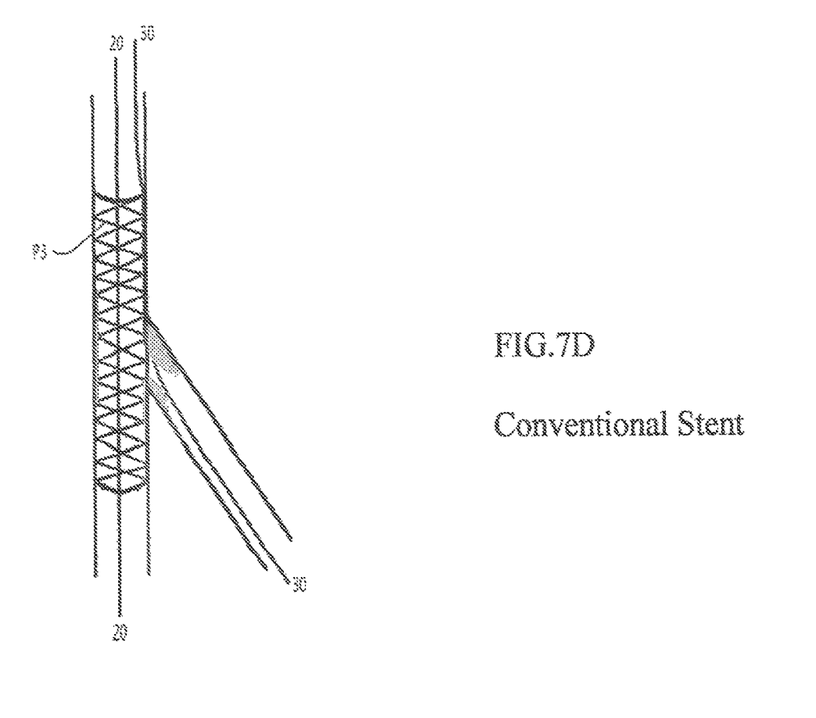

Step 4 is shown in FIG. 7D, wherein the balloon 2P is deflated and pulled out of the vessel. The guidewire 20 is still in the main branches through the lumen of the stent and the guidewire 30 is in the side branch through the space between the vessel wall and the metallic mesh material of the stent (i.e., outside the stent).

Figure 7E:
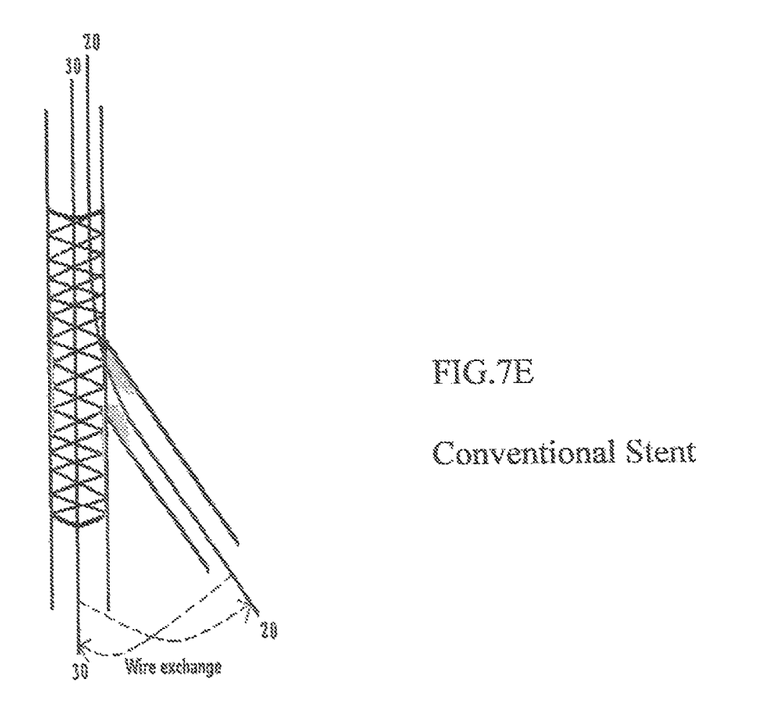

Step 5 is shown in FIG. 7E, in which the guidewire 20 is pulled back and then sent in the lumen of the stent through the metallic mesh to the side branch. The guidewire 30 is also pulled back and then sent through the lumen of the stent to main branch. The process of "wire exchange" is finished, as schematically indicated by the dashed lines in FIG. 7E.

Figure 8A:
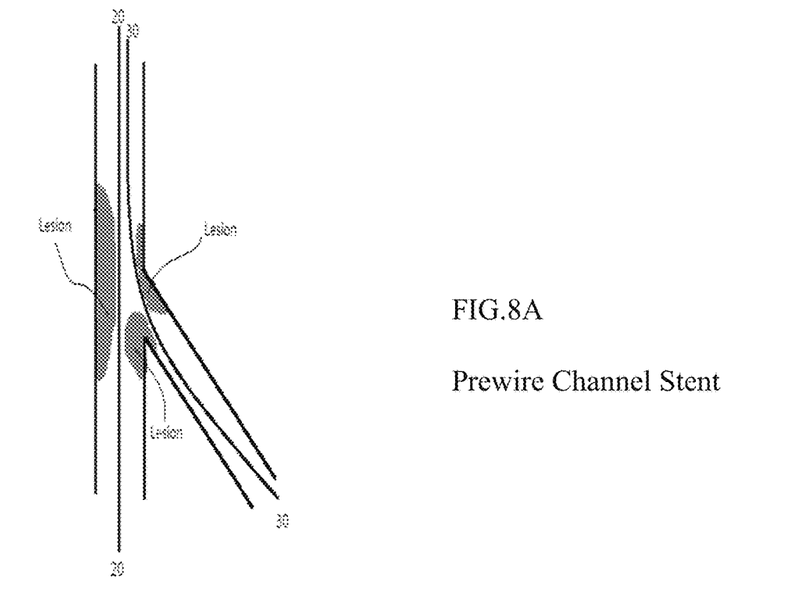
FIGS. 8A-8E illustrate a working example of the procedure of use of the prewire stent of the present invention, and respectively show steps 1-5 for use of the prewire stent of the present invention.

The following illustrates the procedures for use of the prewire channel stent implant 1 of the present invention for a bifurcation lesion in a vessel. Step 1 is shown in FIG. 8A, wherein the guidewire 20 is sent to the main branch and the guidewire 30 is sent to the side branch.

Figure 8B:
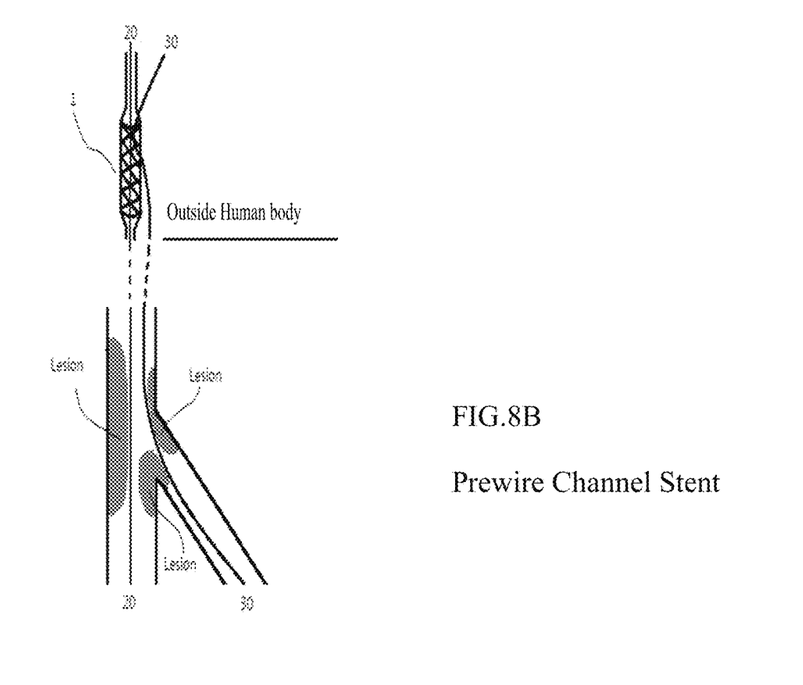

Step 2 is shown in FIG. 8B, wherein the prewire channel stent 1 with the guidewire 30 goes through the channel or space 6 while outside the human body and is then sent through the guidewire 20 (by tracking) to the desired position of the vessels.

Figure 8C:
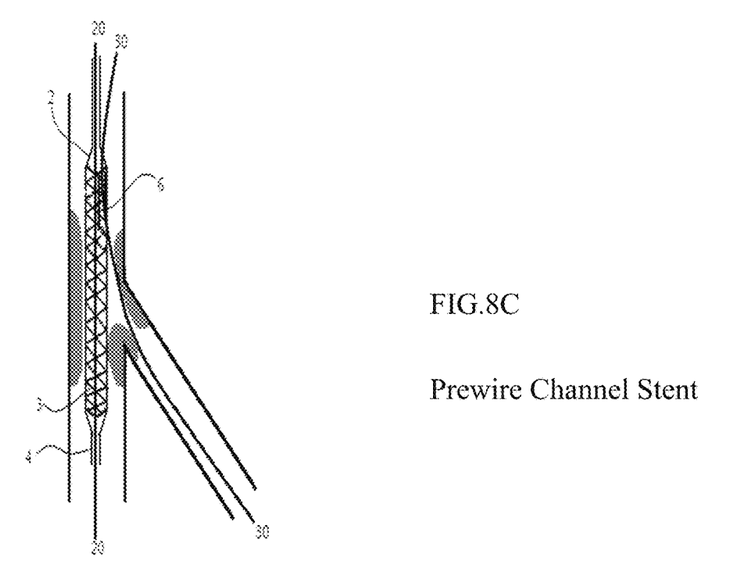

Step 3 is shown in FIG. 8C, wherein the prewire channel stent 1 with the guidewire 30 goes through the channel or space 6 to the desired position of the vessel (at the bifurcation lesion). The balloon 2 is in the deflated status in this view, and the metallic mesh material 3 is mounted in the balloon 2 and the guidewire 30 in the central passage 5 of the catheter 4.

Figure 8D:
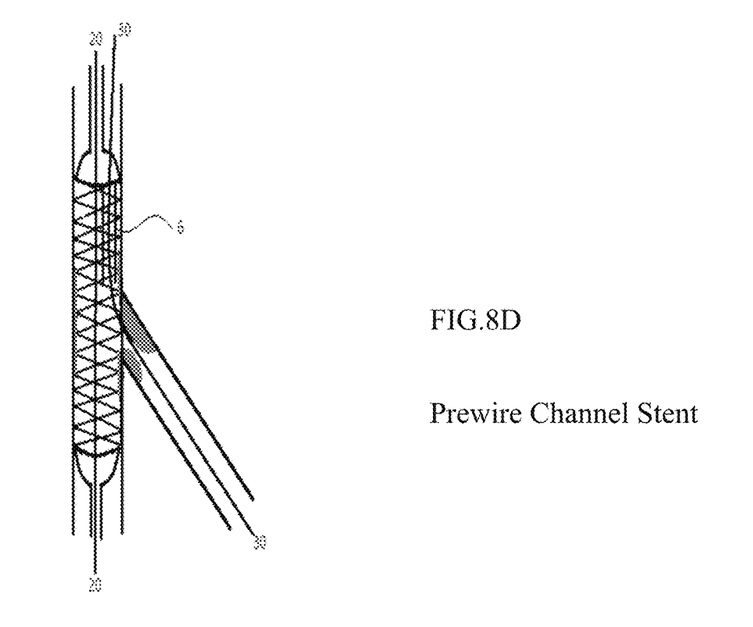

Step 4 is shown in FIG. 8D, wherein the balloon 2 is inflated and the metallic mesh material 3 is dilated. The guidewire 30 from the side branch is in the channel or space 6 and the guidewire 20 is disposed in the main branch.

Figure 8E:
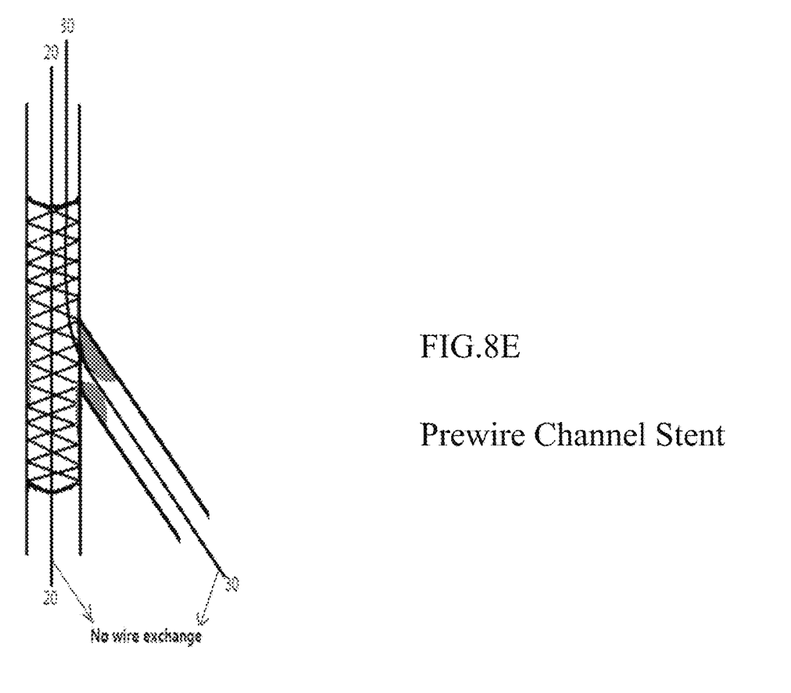

Step 5 is shown in FIG. 8E, wherein the balloon 2 is deflated and withdrawn from the vessel. As seen in FIG. 8E, "wire exchange" is not necessary. This is in contrast to FIG. 7E of the prior device.

The invention being thus described, it will be evident that the same may be varied in many ways by a routineer in the applicable arts. Such variations are not to be regarded as a departure from the spirit and scope of the invention and all such modifications are intended to be included within the scope of the claims.

REFERENCE

1. Jain R K, Padmanabhan T N, Chitnis N. Causes of failure with Szabo technique—an analysis of nine cases. Indian Heart J. 2013 May-June; 65(3):264-8. doi: 10.1016/j.ihj.2013.04.023. Epub 2013 Apr. 10

What is claimed is:

1. A prewire channel stent, comprising:
   a central catheter having a central passage therethrough;
   a balloon disposed around the central catheter, the balloon being inflatable and deflatable, with an inflated status during deployment, and with a deflated status before deployment;
   a metallic mesh material disposed outside said balloon and surrounding said balloon;
   at least one ancillary passage disposed between the metallic mesh material and the balloon, the at least one ancillary passage being adapted to receive a guidewire;
   wherein the mesh material is premounted on the inflatable balloon, and the mesh material is to be expanded when the balloon is inflated during deployment; and
   a plurality of openings formed in the predetermined pattern of the metallic mesh material, the plurality of openings are provided in the at least one ancillary passage at multiple locations along the ancillary passage so that the guidewire can pass into the ancillary passage and exit through one of the openings;
   wherein the ancillary passage has a lining surrounding an interior of boundaries thereof, the ancillary passage has a first boundary formed by the balloon being folded and a second boundary formed by the metallic mesh material.

2. The prewire channel stent of claim 1, wherein the at least one ancillary passage traversing the metallic mesh material at any one of the plurality of openings thereof extends only partway along a length of the metallic mesh material.

3. The prewire channel stent of claim 1, wherein the at least one ancillary passage can accommodate two or more guidewires simultaneously.

* * * * *